(12) United States Patent
Wabnitz et al.

(10) Patent No.: US 8,796,472 B2
(45) Date of Patent: Aug. 5, 2014

(54) MIXTURES OF ITACONIC ACID OR ITACONIC ACID DERIVATIVES AND PRIMARY AMINES FOR PRODUCING 1,3- AND 1,4-ALKYL METHYL PYRROLIDONES

(75) Inventors: Tobias Wabnitz, Mannheim (DE); Rolf Pinkos, Bad Dürkheim (DE); Karl Ott, Plankstadt (DE); Katja Lamm, Mannheim (DE)

(73) Assignee: BASF SE, Ludwigshafen (DE)

( * ) Notice: Subject to any disclaimer, the term of this patent is extended or adjusted under 35 U.S.C. 154(b) by 365 days.

(21) Appl. No.: 13/132,785

(22) PCT Filed: Nov. 24, 2009

(86) PCT No.: PCT/EP2009/065751
§ 371 (c)(1),
(2), (4) Date: Jun. 3, 2011

(87) PCT Pub. No.: WO2010/063617
PCT Pub. Date: Jun. 10, 2010

(65) Prior Publication Data
US 2011/0251119 A1 Oct. 13, 2011

(30) Foreign Application Priority Data

Dec. 4, 2008 (EP) .................................. 08170701

(51) Int. Cl.
*C07D 207/267* (2006.01)
*B01D 53/14* (2006.01)

(52) U.S. Cl.
USPC ............................. 548/543; 548/554; 508/367

(58) Field of Classification Search
None
See application file for complete search history.

(56) References Cited

U.S. PATENT DOCUMENTS

| | | | |
|---|---|---|---|
| 2,604,449 | A | 7/1952 | Bryant et al. |
| 3,044,941 | A | 7/1962 | Nubel et al. |
| 3,448,118 | A | 6/1969 | Chichery et al. |
| 4,731,454 | A | 3/1988 | Otake et al. |
| 5,538,985 | A | 7/1996 | Iizuka et al. |
| 5,753,662 | A | 5/1998 | Peglion et al. |
| 6,476,053 | B1 | 11/2002 | Balganesh et al. |
| 6,525,222 | B2 | 2/2003 | Nouwen et al. |
| 2001/0003136 | A1 | 6/2001 | Nouwen et al. |
| 2004/0158078 | A1 | 8/2004 | Fischer et al. |

FOREIGN PATENT DOCUMENTS

| | | | |
|---|---|---|---|
| CN | 1609089 A | | 4/2005 |
| DE | 1620191 | * | 5/1970 |
| DE | 1620191 A1 | | 5/1970 |
| DE | 19626123 A1 | | 1/1998 |
| EP | 0027022 A1 | | 4/1981 |
| EP | 745598 A1 | | 12/1996 |
| EP | 1106600 A2 | | 6/2001 |
| FR | 89573 E | | 7/1967 |
| JP | H07252218 A | | 10/1995 |
| JP | 2002518324 A | | 6/2002 |

(Continued)

OTHER PUBLICATIONS

Akashi, H., "Chemistry and application of itaconic acid. VI. Syntheses of N-substituted itaconimides and their copolymerization," Kogyo Kagaku Zasshi, 1962, vol. 65, pp. 982-985.

(Continued)

*Primary Examiner* — Necholous Ogden, Jr.
(74) *Attorney, Agent, or Firm* — Drinker Biddle & Reath LLP

(57) ABSTRACT

The present invention relates to a mixture comprising itaconic acid or an itaconic acid derivative and a primary amine of the formula (I)

$$R-NH_2 \qquad (I)$$

where the molar ratio of primary amine to itaconic acid or the itaconic acid derivative is in the range from 0.5:1 to 20:1, wherein the mixture comprises 50 mole percent or less of 4-carboxypyrrolidones of the formula (II), derivatives of the 4-carboxypyrrolidones of the formula (II) and 4-carbamidopyrrolidones of the formula (III) based on the itaconic acid used or the itaconic acid derivative used

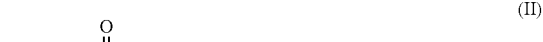

(II)

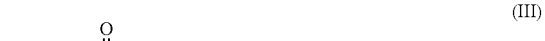

(III)

and in which R is a linear or branched saturated aliphatic radical having 1 to 24 carbon atoms or a saturated cycloaliphatic radical having 3 to 24 carbon atoms.

The invention further provides for the use of the inventive mixtures for preparing 1,3-alkylmethylpyrrolidones and/or 1,4-alkylmethylpyrrolidones, and also a process for preparing 1,3-alkylmethylpyrrolidones and/or 1,4-alkylmethylpyrrolidones.

In addition, the present invention relates to mixtures comprising 1,3-alkylmethylpyrrolidones and/or 1,4-alkylmethylpyrrolidones and 1,3-alkylmethylpyrrolidines, where the proportion of 1,3-alkylmethylpyrrolidines is in the range from 10 to 10 000 ppm, and to mixtures comprising 1,3-alkylmethylpyrrolidone and 1,4-alkylmethylpyrrolidone, wherein the molar ratio of 1,3-alkylmethylpyrrolidone to 1,4-alkylmethylpyrrolidone is in the range from 1:1 to 10:1.

13 Claims, No Drawings

(56) References Cited

FOREIGN PATENT DOCUMENTS

| WO | WO-99/65483 A1 | 12/1999 |
|----|----|----|
| WO | WO-02/04548 A1 | 1/2002 |
| WO | WO-02/102772 A1 | 12/2002 |
| WO | WO-02/102773 A1 | 12/2002 |
| WO | WO-2005/051907 A1 | 6/2005 |
| WO | WO-2005/090447 A2 | 9/2005 |

OTHER PUBLICATIONS

Urzúa, M., et al., "N-1-alkylitaconamic acids-co-styrene copolymers. 1. Syntesis, characterization and monomer reactivity ratios," Journal of Macromolecular Science, Pure and Applied Chemistry, 2000, vol. A37(1 & 2), pp. 37-47.

Watanabe, H., et al., "Polymerization of N-alkyl-substituted itaconimides and N-(alkyl-substituted phenyl)itaconimides and characterization of the resulting polymers," Journal of Polymer Science, Part A: Polymer Chemistry, 1994, vol. 32, No. 11, pp. 2073-2083.

Watanabe, H., et al., "Radical polymerization of N-substituted itaconamic esters and itaconamides," Journal of Polymer Science, Part A: Polymer Chemistry, 1994, vol. 32, No. 11, pp. 2085-2091.

Zilka, A., et al., "Syntheses of amide derivatives of DL-beta-carboxy-gamma-aminobutyric acid," Journal of Organic Chemistry, 1963, vol. 28, No. 8, pp. 2007-2009.

International Preliminary Report on patentability on PCT/EP2009/065751 (PCT application of this application) published Jun. 16, 2011.

\* cited by examiner

MIXTURES OF ITACONIC ACID OR ITACONIC ACID DERIVATIVES AND PRIMARY AMINES FOR PRODUCING 1,3- AND 1,4-ALKYL METHYL PYRROLIDONES

CROSS-REFERENCE TO RELATED APPLICATIONS

This application is a national stage application (under 35 U.S.C. §371) of PCT/EP2009/065751, filed Nov. 24, 2009, which claims benefit of European application 08170701.0 filed Dec. 4, 2008.

BACKGROUND OF THE INVENTION

The present invention relates to mixtures comprising itaconic acid or itaconic acid derivatives and primary amines, and to the use thereof as a starting material for the preparation of 1,3- and 1,4-alkylmethylpyrrolidones.

The present invention further relates to a process for preparing 1,3- and 1,4-alkylmethylpyrrolidones by reacting inventive mixtures with hydrogen in the presence of hydrogenation catalysts. The present invention further provides mixtures comprising 1,3-alkylmethylpyrrolidone and 1,4-alkylmethylpyrrolidone, and for the use of these mixtures.

N-alkylpyrrolidones are important products in the chemical industry, which are used in a multitude of applications.

N-alkylpyrrolidones are thermally stable, chemically substantially inert, colorless, low-viscosity and aprotic solvents with wide usability. For instance, N-methylpyrrolidone (NMP) and N-ethylpyrrolidone (NEP) and the higher homologs are usable as solvents, diluents, extractants, detergents, degreasers, adsorbents and/or dispersants.

NMP finds use in the extraction of pure hydrocarbons in petrochemical processing, in the purification and removal of gases such as acetylene, 1,3-butadiene or isoprene, in aromatics extraction, for example in the Distapex process of LURGI GmbH, in acidic gas scrubbing and in lubricant oil extraction. In addition, NMP can be used as a solvent for polymer dispersions, for example for polyurethane dispersions.

NMP is also a good solvent for many polymers such as polyvinyl chloride (PVC), polyurethanes (PU), acrylates or butadiene-acrylonitrile copolymers, and is used in the processing thereof.

NMP is also used as a detergent in the removal of paint and coating residues, and as a pickling agent and as a detergent for metal, ceramic, glass and plastic surfaces.

NMP is likewise a solvent or cosolvent for the formulation of active ingredients in crop protection.

NEP and other N-alkylpyrrolidones can replace NMP in many applications and, furthermore, in many cases exhibit additionally advantageous properties (WO-A-2005/090447, BASF SE).

The preparation of N-alkylpyrrolidones is known.

N-alkylpyrrolidones can be obtained, for example, by reacting gamma-butyrolactone (γ-BL) with monoalkylamines to release one equivalent of water, for example analogously to Ullmann's Encyclopedia of Industrial Chemistry, Volume A22, 5th ed., p. 459 (1993), or analogously to DE-A-19 626 123 (BASF SE).

It is equally possible to prepare N-alkylpyrrolidones from maleic anhydride or other dicarboxylic acid derivatives and monoethylamines in the presence of hydrogen and a hydrogenation catalyst, for example according to EP-A-745 598 (Bayer AG) oder WO-A-02/102773 (BASF SE).

In addition to N-alkylpyrrolidones, substituted N-alkylpyrrolidones are also known. The substitution allows the application and processing properties of the N-alkylpyrrolidones to be modified.

One example of such a modification is that of N-alkylpyrrolidones with one or more alkyl substituents which are bonded to positions 3 and 4 of the pyrrolidone ring. Alkyl-substituted N-alkylpyrrolidones can be prepared, for example, according to the disclosure of EP-A1-0027022 by reacting alkylamines and hydrogen with substituted cyclic anhydrides/imides in the presence of ruthenium catalysts.

WO-A1-2005051907 discloses the reaction of dicarboxylic acids or derivatives thereof with hydrogen and amines in the presence of ruthenium or osmium catalysts.

U.S. Pat. No. 4,731,454 describes the reduction of cyclic imides over cobalt catalysts to obtain the corresponding N-alkylpyrrolidones.

The reaction of saturated cyclic carboximides or of saturated ammonium salts of the dicarboxylic acids in the presence of carbon-supported noble metal catalysts is disclosed in WO 02/102772.

DE-A1-1620191 describes the reaction of alkylsuccinic acid with primary amines and hydrogen in the presence of a hydrogenation catalyst to give the corresponding N-substituted derivatives of α-pyrrolidones which are alkylated on the carbon atoms in positions 3 and/or 4.

The references cited above disclose only the use of saturated dicarboxylic acids and dicarboxylic acid derivatives, and of dicarboxylic acids or dicarboxylic acid derivatives which have an unsaturated main chain, such as maleic acid and derivatives thereof, as suitable starting materials for the preparation of pyrrolidones. It is not stated that dicarboxylic acids or dicarboxylic acid derivatives which have an unsaturated side chain or even a terminal double bond in the side chain can be converted to the corresponding pyrrolidones.

One example of a dicarboxylic acid having an unsaturated terminal side chain is itaconic acid.

It is known that the reaction of itaconic acid with primary amines forms, in an exothermic reaction, the corresponding 4-carboxypyrrolidones or 4-carbamidopyrrolidones, which form through addition of the primary amines onto the unsaturated side chain (see Imamura et al., Chemical & Pharmaceutical Bulletin (2004), 52(1), 63-73, Paytash et al., Journal of the American Chemical Society (1950), 72, 1415-1416 and Southwick et al., Journal of Organic Chemistry (1956), 21, 1087-1095). Accordingly, the direct reaction of itaconic acid with primary amines and hydrogen to give the corresponding pyrrolidones is not disclosed, since the formation of the 4-carboxypyrrolidones or 4-carbamidopyrrolidones sets in before the hydrogenation to the desired pyrrolidones occurs.

Nitrogen-containing derivatives of itaconic acid, such as the amides or imines thereof, may also react under the conditions of the hydrogenation with addition of the nitrogen onto the double bond to give undesired cyclic by-products.

By virtue of this reactivity, itaconic acid and derivatives thereof differ significantly from their structural isomers citraconic acid and mesaconic acid and derivatives thereof, which have an unsaturated main chain and can therefore be converted by the methods described in the above references to alkylmethylpyrrolidones.

In order nevertheless to be able to use itaconic acid as a starting material for the preparation of methyl-substituted N-alkylpyrrolidones, 2-methylsuccinic acid, according to the teaching of DE-A1-1620191, can be reacted with primary amines with hydrogen in the presence of hydrogenation catalysts. 2-Methylsuccinic acid can in turn be prepared by hydrogenation of itaconic acid (CN-A1-1609089). This means that, however, before the reaction of 2-methylsuccinic acid with primary amines to give pyrrolidones, the 2-methylsuccinic acid starting material has to be obtained in a preceding reaction stage.

BRIEF SUMMARY OF THE INVENTION

It was an object of the present invention to provide a process for preparing 1,3- and 1,4-alkylmethylpyrrolidones, in which itaconic acid or itaconic acid derivatives can be reacted with primary amines and hydrogen with a high selectivity and yield. More particularly, the formation of undesired by-products, especially of 4-carboxypyrrolidone or 4-carbamidopyrrolidone, was to be very substantially avoided. Especially in the case of preparation of 1,3-dimethylpyrrolidone and/or 1,4-dimethylpyrrolidone, the formation of toxic N-methylpyrrolidone was to be avoided. N-methylpyrrolidone can form, for example, through further reactions (decarboxylation/hydrogenation) from 4-carboxypyrrolidone and derivatives thereof.

It was a further object to provide a simplified process for preparing 1,3- and 1,4-alkylmethylpyrrolidones, which is based on itaconic acid but does not necessitate the separate hydrogenation of itaconic acid to the corresponding 2-methylsuccinic acid. A process with high process economy should thus be provided, which is moreover simple to realize in technical terms. A further aim of this invention was the preparation of 1,3- and 1,4-alkylmethylpyrrolidones using itaconic acid or itaconic acid derivatives, which can be prepared on the basis of renewable raw materials. Reverting to renewable raw materials can contribute to sustainment of finite resources and enables sustainable economic activity.

The object is achieved by providing a mixture comprising itaconic acid or an itaconic acid derivative and a primary amine of the formula (I)

R—NH$_2$  (I)

where the molar ratio of primary amine to itaconic acid or the itaconic acid derivative is in the range from 0.5:1 to 20:1, wherein the mixture comprises 50 mole percent or less of 4-carboxypyrrolidones of the formula (II), derivatives of the 4-carboxypyrrolidones of the formula (II) and 4-carbamidopyrrolidones of the formula (III) based on the itaconic acid used or the itaconic acid derivative used

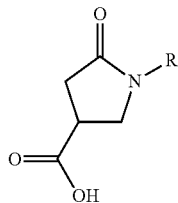

(II)

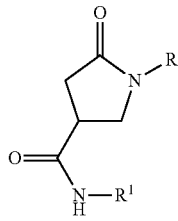

(III)

and in which R is a linear or branched saturated aliphatic radical having 1 to 24 carbon atoms or a saturated cycloaliphatic radical having 3 to 24 carbon atoms.

DETAILED DESCRIPTION OF THE INVENTION

The inventive mixture comprises a primary amine of the general formula (I)

R—NH$_2$  (I)

in which R is a linear or branched saturated aliphatic radical having 1 to 24 carbon atoms, preferably $C_{1-12}$-alkyl, such as methyl, ethyl, n-propyl, isopropyl, n-butyl, iso-butyl, sec-butyl, tert-butyl, n-pentyl, isopentyl, sec-pentyl, neopentyl, 1,2-dimethylpropyl, n-hexyl, isohexyl, sec-hexyl, cyclopentylmethyl, n-heptyl, isoheptyl, cyclohexylmethyl, n-octyl, 2-ethylhexyl, n-nonyl, isononyl, n-decyl, isodecyl, n-undecyl, n-dodecyl, isododecyl, more preferably $C_{1-8}$-alkyl, such as methyl, ethyl, n-propyl, isopropyl, n-butyl, isobutyl, sec-butyl, tert-butyl, n-pentyl, n-hexyl, n-octyl and 2-ethylhexyl, most preferably $C_{1-4}$-alkyl, such as methyl, ethyl, n-propyl, isopropyl, n-butyl, isobutyl, sec-butyl, tert-butyl, especially preferably methyl, or a saturated cycloaliphatic radical having 3 to 24 carbon atoms, preferably $C_{4-8}$-cycloalkyl, such as cyclobutyl, cyclopentyl, cyclohexyl, cycloheptyl and cyclooctyl, more preferably cyclopentyl and cyclohexyl.

Preferred primary amines are methylamine, ethylamine, n-propylamine, iso-propylamine, n-butylamine, isobutylamine, sec-butylamine, tert-butylamine, n-pentylamine, isopentylamine and 2-ethylhexylamine.

Very particularly preferred primary amines are methylamine, ethylamine, n-propylamine, isopropylamine, n-butylamine, isobutylamine, sec-butylamine and tert-butylamine, especially methylamine.

The inventive mixtures further comprise itaconic acid or an itaconic acid derivative.

In a particularly preferred embodiment, the inventive mixture comprises itaconic acid. Itaconic acid is preferably prepared on the basis of renewable raw materials.

Itaconic acid can be obtained, for example, by distilling lemon peel.

In general, itaconic acid is produced commercially by fermenting carbohydrates from unrefined cane or beet sugar or from molasses. Typically, use of the enzyme *Aspergillus terreus* or *Aspergillus itaconicus* (Jakubowska, in Smith and Pateman (eds.), Genetics and Physiology of *Aspergillus*, London: Academic Press 1977; Miall, in Rose (ed.), Economic Microbiology, Vol. 2, p. 47-119, London: Academic Press 1978) forms itaconic acid from citric acid, which is formed in the citric acid cycle. The citric acid is generally first converted by the aconitate hydratase to cis-aconitic acid, which is then decarboxylated by the aconitate decarboxylase to itaconic acid (U.S. Pat. No. 3,044,941). The presence or the absence of the structurally isomeric citraconic acid and mesaconic acid, which can be obtained from itaconic acid, in the inventive mixtures is uncritical.

The inventive mixture may also comprise an itaconic acid derivative.

The itaconic acid derivative is preferably an itaconic ester. Itaconic acid can be esterified by known methods.

Cowie et al. (J. M. G. Cowie et al., Polymer 18 (1977), 612-616) disclose the acid-catalyzed esterification of itaconic acid, in which a product mixture of the diester of itaconic acid and the corresponding 4-alkyl itaconate is obtained. The 4-alkyl itaconate generally also forms as the main product in the esterification of the anhydride, since the 4 position is more reactive than the 2 position.

Preferred diesters of itaconic acid are dimethyl itaconate, diethyl itaconate, di-n-propyl itaconate, di-n-butyl itaconate, di-n-pentyl itaconate, di-n-2-methylpentyl itaconate, di-n-hexyl itaconate, and di-2-ethylhexyl itaconate.

Preferred monoesters of itaconic acid are 4-methyl itaconate, 4-ethyl itaconate, 4-n-propyl itaconate, and 4-n-butyl itaconate, 4-n-pentyl itaconate, 4-(2-methylpentyl)itaconate, 4-n-hexyl itaconate and 4-(2-ethylhexyl)itaconate.

A further preferred itaconic acid derivative is itaconamide.

The synthesis of itaconamides is described in the thesis by Christine Rüdiger ("Synthesen and Untersuchungen zum Polymerisationsverhalten von Itaconsäurederivaten" [Syntheses and Studies of the Polymerization Behavior of itaconic acid derivatives], University of Wuppertal, page 38 (http://elpub.bib.uni-wuppertal.de/edocs/dokumente/fb09/diss2000/ruediger; internal&action=buildframes.action)).

The starting material for the synthesis of the itaconamides is generally itaconic anhydride, which is reacted in THF with the appropriate primary amine. The product can be isolated by recrystallization, for example from cyclohexane.

In general, the monoamides of itaconic acid (itaconic acid 4-amides) are obtained, since, as explained above, the 4 position is more reactive than the 2 position. However, it is also possible to use diamides or mixtures of mono- and diamides of itaconic acid.

Itaconimides can also be used as preferred itaconic acid derivatives in the inventive mixture.

Other itaconic acid derivatives which can be used in the process are itaconic acid derivatives which are chemically similar in behavior to one or more of the aforementioned itaconic acid derivatives, for example the corresponding itaconyl halides such as itaconyl chloride or itaconyl bromide.

However, the itaconic acid derivatives used may also be salts of itaconic acid or mixtures of salts of itaconic acid.

Salts of itaconic acid are, for example, metal salts of itaconic acid, such as alkali metal salts of itaconic acid, alkaline earth metal salts of itaconic acid, aluminum salts of itaconic acid or iron salts of itaconic acid.

However, the salts of itaconic acid used may also be ammonium salts of itaconic acid or alkylammonium salts of itaconic acid.

The molar ratio of amine to itaconic acid or the itaconic acid derivative used is, according to the invention, 0.5:1 to 20:1.

When itaconic acid or monoesters of itaconic acid or diesters of itaconic acid are used, the molar ratio of amine to itaconic acid or itaconic ester is preferably 1:1 to 20:1, more preferably 1.5:1 to 10:1 and more preferably 2:1 to 8:1.

When the itaconic acid derivative used is the monoamide of itaconic acid or the monoimide of itaconic acid, the molar ratio of amine to the monosubstituted derivatives of itaconic acid mentioned is preferably 0.5:1 to 20:1, more preferably 1:1 to 10:1 and most preferably 2:1 to 8:1.

When the itaconic acid derivative used is the diamide of itaconic acid or the diimide of itaconic acid, the molar ratio of amine to the disubstituted derivatives of itaconic acid mentioned is preferably 0.5:1 to 20:1, more preferably 0.5:1 to 10:1 and most preferably 1:1 to 8:1.

The inventive mixtures comprise a proportion of 4-carboxypyrrolidones of the formula (II), of derivatives of the 4-carboxypyrrolidones of the formula (II) and of 4-carbamidopyrrolidones of the formula (III) of less than 50 mole percent based on the itaconic acid used or the itaconic acid derivative used, preferably less than 30 mole percent, more preferably less than 10 mole percent, even more preferably less than 5 mole percent and especially preferably less than 1 mole percent, based in each case on the itaconic acid used or the itaconic acid derivative used.

In general, 4-carboxypyrrolidones of the formula (II) are present in the inventive mixture not in the form of the free acid but as corresponding derivatives of the 4-carboxypyrrolidones of the formula (II) which can form in the inventive mixture.

Such derivatives of the 4-carboxypyrrolidones of the formula (II) can be illustrated by the general formula (IX)

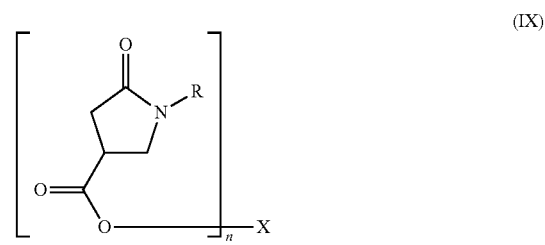

(IX)

where n is an integer from 1 to 4
and X is H, R, a metal M or $NH_3R$, where R is as defined above.

n is preferably an integer from 1 to 2; n is more preferably 1.

X may be an organic R radical, where R is as defined above.

M is preferably a mono- to tetravalent metal, preferably a metal of the alkali metal group or alkaline earth metal group, such as Ca or Mg, more preferably of the alkali metal group, such as Li, Na or K.

X is more preferably $NH_3R$ where R is as defined above.

When X is M or $NH_3R$, the compound of the general formula (VIII) is preferably present in salt form, in which case the negative charge is preferably localized on the carboxylate group ($COO^-$) and the positive charge preferably on the substituent X, for example as $M^+$ or $N+RH_3$.

The mixtures of itaconic acid or itaconic acid derivatives and primary amines known in the prior art comprise a relatively high proportion of 4-carboxypyrrolidones of the formula (II) or 4-carbamidopyrrolidones of the formula (III), since these compounds, as described above, form spontaneously through addition of the primary amines onto the double bond of the itaconic acid.

It has been found that inventive mixtures of primary amine and itaconic acid or itaconic acid derivatives with a relatively small proportion of 4-carboxypyrrolidones of the formula (II), derivatives of the 4-carboxypyrrolidones of the formula (II) and 4-carbamidopyrrolidones of the formula (III) are obtainable by contacting the primary amine with the itaconic acid or the itaconic acid derivative, the temperature during the contacting being 100° C. or less.

Accordingly, the present invention relates to a process for preparing a mixture comprising itaconic acid or an itaconic acid derivative and a primary amine of the formula (I)

$R-NH_2$ (I)

where the molar ratio of primary amine to itaconic acid or the itaconic acid derivative is in the range from 0.5:1 to 20:1, wherein the mixture comprises 50 mole percent or less of 4-carboxypyrrolidones of the formula (II), derivatives of the 4-carboxypyrrolidones of the formula (II) and 4-carbamidopyrrolidones of the formula (III), based on the itaconic acid used or the itaconic acid derivative used,

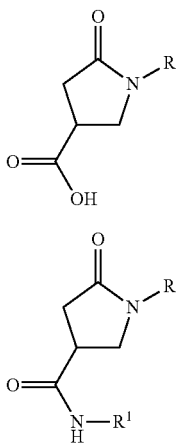

(II)

(III)

and in which R is a linear or branched saturated aliphatic radical having 1 to 24 carbon atoms or a saturated cycloaliphatic radical having 3 to 24 carbon atoms, wherein the primary amine is contacted with the itaconic acid or the itaconic acid derivative, the temperature during the contacting being 100° C. or less.

The itaconic acid or the itaconic acid derivative is contacted with the primary amine preferably by mixing the two components.

The mixing of itaconic acid or the itaconic acid derivative and the primary amine should preferably afford a homogeneous mixture. The homogenization can be effected, for example, by intensive stirring, preferably with a stirrer, for example a planetary stirrer, anchor stirrer, beam stirrer, propeller, paddle stirrer, dissolver disks or Intermig stirrer. Further suitable stirrer configurations are known to those skilled in the art.

According to the invention, the temperature during the contacting of itaconic acid or the itaconic acid derivative with the primary amine is 100° C. and less, preferably 75° C. and less, even more preferably 50° C. and less, especially preferably 25° C. and less. The temperature during the contacting of itaconic acid or the itaconic acid derivative with the primary amine is preferably in the range from −10 to 100° C., preferably in the range from −5 to 75° C., more preferably in the range from 0 to 50° C. and especially preferably in the range from 0 to 25° C.

Typically, the contacting of itaconic acid or the itaconic acid derivative and primary amine is performed in a cooled jacketed vessel.

The primary amine and itaconic acid or the itaconic acid derivative are contacted preferably in a solvent. The solvent should have sufficient miscibility with the primary amine used.

The solvent should preferably also have good miscibility with the mixture of itaconic acid or the itaconic acid derivative and the primary amine. Such a solvent can be found by dissolution tests of primary amine and solvent at the appropriate temperatures, at which the primary amine is contacted with the itaconic acid or the itaconic acid derivative.

Preferred solvents are water, methanol, ethanol, n-/isopropanol, n-/isobutanol, THF, dimethylformamide, dimethylacetamide, alkylmethylpyrrolidones or N-alkylpyrrolidones. Particular preference is given to using water as the solvent.

The proportion of itaconic acid or the itaconic acid derivative in the solvent is generally 5 to 95% by weight based on the solvent used, preferably 10 to 70% by weight and more preferably 20 to 60% by weight, based in each case on the solvent used. In general, the primary amine is initially charged and the itaconic acid or the itaconic acid derivative is added.

As described above, the primary amine can be initially charged together with a solvent. The itaconic acid or the itaconic acid derivative may likewise be dissolved in a solvent. This solvent is preferably the same as that used for the dissolution of the primary amine. However, it may also be another solvent, provided that the two solvents are miscible with one another. The itaconic acid or the itaconic acid derivative may, however, also be added in solid form to the primary amine or to the mixture of primary amine and solvent.

In a particularly preferred embodiment, the inventive mixture comprises a salt of the general formula $[A^{2-}]\,[B^+][C^+]$, where $[A^{2-}]$ is an anion of the formula (IV)

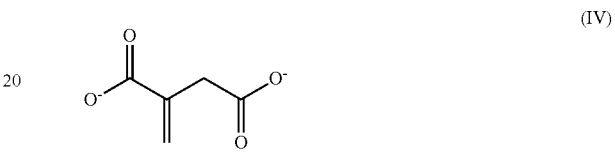

(IV)

$[B^+]$ is a cation of the formula (V)

(V)

$[C^+]$ is a cation of the formula (V) or $[H^+]$ and R is as defined above.

The ammonium salt of the itaconic acid with the general formula $[A^{2-}]\,[B^+][C^+]$ may be present in solvated or dissociated form, but may also be present in solid salt form.

The ammonium salt of the itaconic acid of the general formula $[A^{2-}]\,[B^+][C+]$ is obtainable by contacting itaconic acid and a primary amine, the temperature during the contacting being 100° C. or less.

The molar ratio of primary amine to itaconic acid is generally 1:1 to 2:1.

When the ratio of primary amine to itaconic acid is 1:1, generally the monosalt of itaconic acid is formed ($[B^+]$=cation of the formula (V) and $[C^+]=[H^+]$).

When the ratio of primary amine to itaconic acid is 2:1, generally the disalt of itaconic acid is formed ($[B^+]$ and $[C^+]$= cation of the formula (V)).

When the molar ratio of primary amine to itaconic acid is between 1:1 and 2:1, generally mixtures of the monosalt and of the disalt are obtained.

The molar ratio of primary amine to itaconic acid may also be more than 2:1. In general, in that case, a solution or mixture of the inventive ammonium salt of itaconic acid and excess primary amine is obtained. The molar ratio of amine to itaconic acid is preferably 1:1 to 20:1, more preferably 1.5:1 to 10:1 and more preferably 2:1 to 8:1.

The itaconic acid is contacted with the primary amine preferably by mixing the two components. The mixing of itaconic acid and the primary amine should preferably afford a homogeneous mixture. The homogenization can be effected, for example, by intensive stirring, preferably with a stirrer, for example a planetary stirrer, anchor stirrer, beam stirrer, propeller, paddle stirrer, dissolver disks or Intermig stirrer. Further suitable stirrer configurations are known to those skilled in the art.

According to the invention, the temperature during the contacting of itaconic acid with the primary amine is 100° C. and less, preferably 75° C. and less, even more preferably 50° C. and less, especially preferably 25° C. and less. The temperature during the contacting of itaconic acid with the primary amine is preferably in the range from −10 to 100° C., preferably in the range from −5 to 75° C., more preferably in the range from 0 to 50° C. and especially preferably in the range from 0 to 25° C.

Typically, the contacting of itaconic acid and primary amine is performed in a cooled jacketed vessel.

In a particularly preferred embodiment, primary amine and itaconic acid are contacted in a solvent. The solvent should have a sufficient miscibility with the primary amine used.

The solvent should preferably also have a good miscibility with the mixture of itaconic acid and primary amine. Such a solvent can be found by dissolution tests of primary amine and solvent at the appropriate temperatures, at which the primary amine is contacted with the itaconic acid.

Preferred solvents are water, methanol, ethanol, n-/isopropanol, n-/isobutanol, THF, dimethylformamide, dimethylacetamide, alkylmethylpyrrolidones and N-alkylpyrrolidones.

Particular preference is given to using water as the solvent.

The proportion of itaconic acid in the solvent is generally 5 to 95% by weight, based on the solvent used, preferably 10 to 70% by weight and more preferably 20 to 60% by weight, based in each case on the solvent used.

In general, the primary amine is initially charged and the itaconic acid is added.

As described above, the primary amine can be initially charged together with a solvent.

The itaconic acid may likewise be dissolved in a solvent. This solvent is preferably the same as that used for the dissolution of the primary amine. However, it may also be another solvent, provided that the two solvents are miscible with one another.

However, the itaconic acid can also be added in solid form to the primary amine or to the mixture of primary amine and solvent.

The inventive ammonium salts of itaconic acid are typically present as a mixture with the solvent or excess primary amine in solvated or dissociated form.

The inventive ammonium salts of itaconic acid can be isolated, for example by precipitating the salts by adding a liquid which has a low solubility for the itaconic acid salts.

The salts can also be isolated by evaporating the solvent, in which case the temperature in the course of evaporation should not be more than 100° C., preferably in the range from 0 to 100° C., more preferably in the range from 5 to 75° C. and most preferably in the range from 10 to 50° C., in order to prevent the formation of by-products in the evaporation.

In a very particularly preferred embodiment, however, the mixture of solvent and itaconic acid salt, the itaconic acid salt preferably being present in dissociated form, will be used directly in the hydrogenation without further workup.

The inventive mixtures comprising itaconic acid or an itaconic acid derivative and primary amines can also be prepared in the presence of hydrogen. When the inventive mixtures are prepared in the presence of hydrogen, the temperature in the preparation of the mixtures should be selected such that no formation of the undesired by-products occurs. Preference is therefore given to preparing the mixture in the presence of hydrogen at 100° C. and less, preferably 75° C. and less, more preferably at 50° C. and less, especially preferably at 25° C. and less. The temperature during the contacting of itaconic acid or the itaconic acid derivative with the primary amine in the presence of hydrogen is preferably in the range from −10 to 100° C., preferably in the range from −5 to 75° C., more preferably in the range from 0 to 50° C. and especially preferably in the range from 0 to 25° C.

The inventive mixtures can be stored before being processed further. They are preferably stored under conditions under which a conversion of the mixture to the undesired by-products 4-carboxypyrrolidone, derivatives of 4-carboxypyrrolidone or 4-carbamidopyrrolidone is avoided.

Preference is given to storing them at temperatures of −10 to 100° C., more preferably at temperatures of −5 to 75° C. and more preferably at temperatures of 0 to 50° C., especially at ambient temperature, in order to reduce the formation of the by-produced 4-carboxypyrrolidones of the formula (II), derivatives of the 4-carboxypyrrolidones of the formula (II) or 4-carbamidopyrrolidones of the formula (III).

One advantage of the present invention is that stable mixtures of itaconic acid or itaconic acid derivatives and primary amines can be provided, in which the formation of undesired by-products, such as 4-carboxypyrrolidone, derivatives of 4-carboxypyrrolidone of the formula (II) or 4-carbamidopyrrolidone, is very substantially prevented. These mixtures are stable at ambient temperature and can thus be stored and transported without an increased level of technical complexity. The inventive mixtures which comprise only a low proportion of 4-carboxypyrrolidone or 4-carbamidopyrrolidone thus constitute a suitable novel starting material for the preparation of 1,3- and 1,4-alkylmethylpyrrolidones. Proceeding from this, starting material, the corresponding 1,3- and 1,4-alkylmethylpyrrolidones can be obtained in high selectivity and yield, based on the itaconic acid or itaconic acid derivatives used.

The present invention accordingly further provides for the use of a mixture comprising itaconic acid or an itaconic acid derivative and a primary amine of the formula (I)

R—NH₂ (I)

where the molar ratio of primary amine to itaconic acid or the itaconic acid derivative is in the range from 0.5:1 to 20:1, wherein the mixture comprises 50 mole percent or less of 4-carboxypyrrolidones of the formula (II), derivatives of the 4-carboxypyrrolidones of the formula (II) and 4-carbamidopyrrolidones of the formula (III), based on the itaconic acid used or the itaconic acid derivative used,

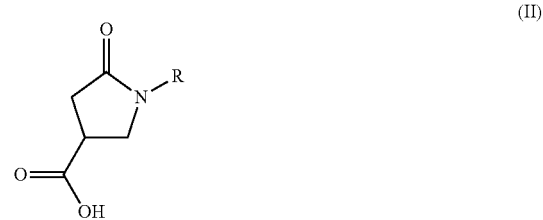

(II)

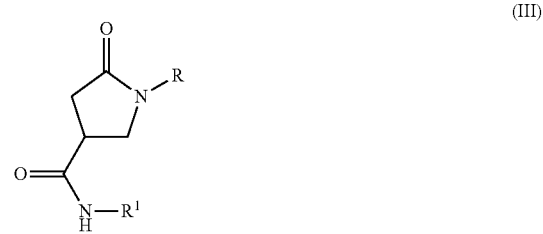

(III)

for preparing 1,3-alkylmethylpyrrolidones of the general formula (VI) and/or 1,4-alkylmethylpyrrolidones of the general formula (VII)

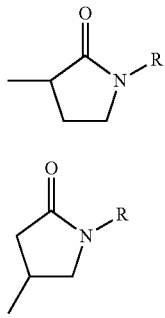

(VI)

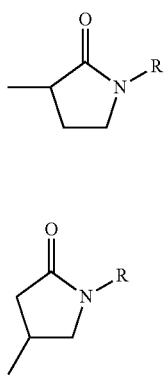

(VII)

where R is as defined above.

The present invention further relates to a process for preparing 1,3-alkylmethylpyrrolidones of the general formula (VI) and/or 1,4-alkylmethylpyrrolidones of the general formula (VII)

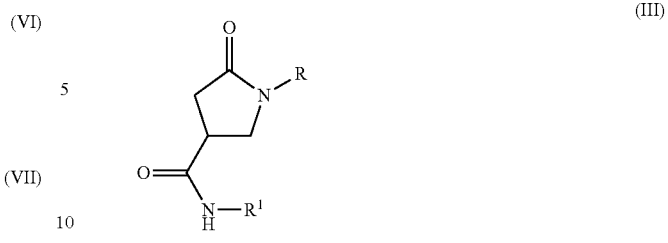

by reacting a mixture comprising itaconic acid or an itaconic acid derivative and a primary amine of the formula (I) with hydrogen in the presence of a hydrogenation catalyst

R—NH$_2$ (I)

where the molar ratio of primary amine to itaconic acid or the itaconic acid derivative is in the range from 0.5:1 to 20:1 and the mixture comprises 50 mole percent or less of 4-carboxypyrrolidones of the formula (II), derivatives of the 4-carboxypyrrolidones of the formula (II) and 4-carbamidopyrrolidones of the formula (III) based on itaconic acid or itaconic acid derivative, and

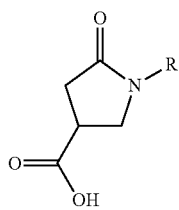

(II)

(III)

in which R is as defined above.

The process according to the invention takes place in the presence of a hydrogenation catalyst. The hydrogenation catalysts used may in principle be all hydrogenation catalysts which comprise nickel, cobalt, iron, copper, ruthenium, chromium, manganese, molybdenum, tungsten, rhenium and/or other metals of groups 8 and/or 9 and/or 10 and/or 11 of the Periodic Table of the Elements (Periodic Table in the IUPAC version dated Jun. 22, 2007).

Preference is given to using hydrogenation catalysts which comprise ruthenium, rhodium, cobalt and/or nickel. Particular preference is given to catalysts which comprise rhodium, ruthenium and/or cobalt. Very particular preference is given to catalysts which comprise rhodium.

The abovementioned hydrogenation catalysts can typically be doped with promoters, for example with chromium, iron, cobalt, manganese, thallium, molybdenum, titanium and/or phosphorus.

The catalytically active metals can be used in the form of unsupported catalysts or on supports. Useful supports of this kind include, for example, carbon such as graphite, carbon black and/or activated carbon, aluminum oxide (gamma, delta, theta, alpha, kappa, chi or mixtures thereof), silicon dioxide, zirconium dioxide, zeolites, aluminosilicates or mixtures thereof.

The catalytically active metals can be used, for example, in the form of sponge catalysts, so-called Raney catalysts. The Raney catalysts used are preferably Raney cobalt catalysts, Raney nickel catalysts and/or Raney copper catalysts.

Raney hydrogenation catalysts are prepared, for example, by treating an aluminum-metal alloy with concentrated sodium hydroxide solution, which leaches out the aluminum and forms a metallic sponge. The preparation of Raney hydrogenation catalysts is described, for example, in the Handbook of Heterogeneous Catalysis (M. S. Wainright in G. Ertl, H. Knózinger, J. Weitkamp (eds.), Handbook of Heterogeneous Catalysis, Vol. 1, Wiley-VCH, Weinheim, Germany 1997, page 64 ff.). Such catalysts are obtainable, for example, as Raney® catalysts from Grace or as Sponge Metal® catalysts from Johnson Matthey.

The hydrogenation catalysts usable in the process according to the invention can also be prepared by reducing catalyst precursors.

The catalyst precursor comprises an active material which comprises one or more catalytically active components and optionally a support material.

The catalytically active components are oxygen compounds of the metals of the abovementioned active metals, for example the metal oxides or hydroxides thereof (if appropriate examples), such as CoO, NiO, Mn$_3$O$_4$, CuO, RuO(OH)$_x$ and/or mixed oxides thereof.

In the context of this application, the term "catalytically active components" is used for the abovementioned oxygen-containing metal compounds, but is not intended to imply that these oxygen compounds themselves are already catalytically active. The catalytically active components generally have catalytic activity in the inventive reaction only on completion of reduction.

The catalyst precursors can be prepared by known processes, for example by precipitation, precipitative application or impregnation.

In a preferred embodiment, catalyst precursors which are prepared by impregnating support materials are used in the process according to the invention (impregnated catalyst precursors).

The support materials used in the impregnation can, for example, be used in the form of powders or shaped bodies, such as extrudates, tablets, spheres or rings. Support material suitable for fluidized bed reactors is preferably obtained by spray drying. Useful support materials include, for example, carbon such as graphite, carbon black and/or activated carbon, aluminum oxide (gamma, delta, theta, alpha, kappa, chi or mixtures thereof), silicon dioxide, zirconium dioxide, zeolites, aluminosilicates or mixtures thereof.

The abovementioned support materials can be impregnated by the customary methods (A. B. Stiles, Catalyst Manufacture—Laboratory and Commercial Preparations, Marcel Dekker, New York, 1983), for example by applying a metal salt solution in one or more impregnation stages. Useful metal salts generally include water-soluble metal salts, such as the nitrates, acetates or chlorides of the corresponding catalytically active components or doping elements, such as cobalt nitrate or cobalt chloride. Thereafter, the impregnated support material is generally dried and if appropriate calcined. The impregnation can also be effected by the so-called "incipient wetness method", in which the support material is moistened with the impregnating solution up to a maximum of saturation according to its water absorption capacity. However, the impregnation can also be effected in supernatant solution.

In the case of multistage impregnation processes, it is appropriate to dry and if appropriate to calcine between individual impregnation steps. Multistage impregnation can be employed advantageously when the support material is to be contacted with metal salts in a relatively large amount.

To apply a plurality of metal components to the support material, the impregnation can be effected simultaneously with all metal salts or in any desired sequence of the individual metal salts in succession.

In a further preferred embodiment, catalyst precursors are prepared by means of a coprecipitation of all of their components. To this end, in general, a soluble compound of the appropriate active component, of the doping elements, and if appropriate a soluble compound of a support material are admixed with a precipitant in a liquid under hot conditions and with stirring until the precipitation is complete.

The liquid used is generally water.

Useful soluble compounds of the active components typically include the appropriate metal salts, such as the nitrates, sulfates, acetates or chlorides, of the metals of groups 8 and/or 9 and/or 10 and/or 11 of the Periodic Table of the Elements (Periodic Table in the IUPAC version dated Jun. 22, 2007).

The water-soluble compounds of a support material used are generally water-soluble compounds of Ti, Al, Zr, Si etc., for example the water-soluble nitrates, sulfates, acetates or chlorides of these elements.

The water-soluble compounds of the doping elements used are generally water-soluble compounds of the doping elements, for example the water-soluble nitrates, sulfates, acetates or chlorides of these elements.

Catalyst precursors can also be prepared by precipitative application.

Precipitative application is understood to mean a preparation method in which a sparingly soluble or insoluble support material is suspended in a liquid and then soluble compounds, such as soluble metal salts, of the appropriate metal oxides are added, which are then precipitated onto the suspended support by adding a precipitant (for example, described in EP-A2-1 106 600, page 4, and A. B. Stiles, Catalyst Manufacture, Marcel Dekker, Inc., 1983, page 15).

Useful sparingly soluble or insoluble support materials include, for example, carbon compounds such as graphite, carbon black and/or activated carbon, aluminum oxide (gamma, delta, theta, alpha, kappa, chi or mixtures thereof), silicon dioxide, zirconium dioxide, zeolites, aluminosilicates or mixtures thereof.

The support material is generally present in the form of powder or spall.

The liquid used, in which the support material is suspended, is typically water.

Useful soluble compounds include the aforementioned soluble compounds of the active components or of the doping elements.

In the precipitation reactions, the kind of soluble metal salts used is generally uncritical. Since the principal factor in this procedure is the water solubility of the salts, one criterion is their good water solubility, which is required to prepare these comparatively highly concentrated salt solutions. It is considered to be obvious that, in the selection of the salts of the individual components, of course only salts with those anions which do not lead to disruption, whether by causing undesired precipitation reactions or by complicating or preventing the precipitation by complex formation, are selected.

Typically, in the precipitation reactions, the soluble compounds are precipitated as sparingly soluble or insoluble basic salts by adding a precipitant.

The precipitants used are preferably alkalis, especially mineral bases, such as alkali metal bases. Examples of precipitants are sodium carbonate, sodium hydroxide, potassium carbonate or potassium hydroxide.

The precipitants used may also be ammonium salts, for example ammonium halides, ammonium carbonate, ammonium hydroxide or ammonium carboxylates.

The precipitation reactions can be performed, for example, at temperatures of 20 to 100° C., preferably 30 to 90° C., especially at 50 to 70° C.

The precipitates obtained in the precipitation reactions are generally chemically inhomogeneous and generally comprise mixtures of the oxides, oxide hydrates, hydroxides, carbonates and/or hydrogencarbonates of the metals used. It may be found to be favorable for the filterability of the precipitates when they are aged, i.e. when they are left alone for a certain time after the precipitation, if appropriate under hot conditions or while passing air through.

The precipitates obtained by these precipitation processes are typically processed by washing, drying, calcining and conditioning them.

After washing, the precipitates are generally dried at 80 to 200° C., preferably 100 to 150° C., and then calcined.

The calcination is performed generally at temperatures between 300 and 800° C., preferably 400 to 600° C., especially at 450 to 550° C.

After the calcination, the catalyst precursors obtained by precipitation reactions are typically conditioned.

The conditioning can be effected, for example, by adjusting the precipitated catalyst to a particular particle size by grinding.

After the grinding, the catalyst precursor obtained by precipitation reactions can be mixed with shaping assistants such as graphite or stearic acid, and processed further to shaped bodies.

Common processes for shaping are described, for example, in Ullmann [Ullmann's Encyclopedia Electronic Release 2000, chapter: "Catalysis and Catalysts", pages 28-32] and by Ertl et al. [Ertl, Knozinger, Weitkamp, Handbook of Heterogeneous Catalysis, VCH Weinheim, 1997, pages 98 ff].

As described in the references cited, the process for shaping can provide shaped bodies in any three-dimensional shape, for example round, angular, elongated or the like, for example in the form of extrudates, tablets, granule, spheres, cylinders or grains. Common processes for shaping are, for example, extrusion, tableting, i.e. mechanical pressing, or pelletizing, i.e. compacting by circular and/or rotating motions. The conditioning or shaping is generally followed by a heat treatment. The temperatures in the heat treatment typically correspond to the temperatures in the calcination.

The catalyst precursors obtained by precipitation reactions comprise the catalytically active components in the form of a mixture of oxygen compounds thereof, i.e. especially as oxides, mixed oxides and/or hydroxides. The catalyst precursors thus prepared can be stored as such.

Before they are used as hydrogenation catalysts, catalyst precursors which, as described above, have been obtained by impregnation or precipitation are generally prereduced by treatment with hydrogen after the calcination or conditioning.

For the prereduction, the catalyst precursors are generally first exposed to a nitrogen-hydrogen atmosphere at 150 to 200° C. over a period of 12 to 20 hours, and then treated in a hydrogen atmosphere at 200 to 400° C. for another up to approx. 24 hours. This prereduction reduces a portion of the oxygen-containing metal compounds present in the catalyst precursors to the corresponding metals, such that they are present together with the different kinds of oxygen compounds in the active form of the hydrogenation catalyst.

In a preferred embodiment, the prereduction of the catalyst precursor is undertaken in the same reactor in which the hydrogenation is subsequently performed.

The hydrogenation catalyst thus formed can be handled and stored under an inert gas such as nitrogen after the prereduction, or be used for the hydrogenation catalyst under an inert liquid, for example an alcohol, water or the product of the particular reaction. However, the hydrogenation catalyst, after the prereduction, can also be passivated with an oxygen-comprising gas stream such as air or a mixture of air with nitrogen, i.e. provided with a protective oxide layer.

The storage of hydrogenation catalysts which have been obtained by prereduction of the catalyst precursors under inert substances or the passivation of the hydrogenation catalyst enables uncomplicated and safe handling and storage of the catalyst. If appropriate, the hydrogenation catalyst then has to be freed of the inert liquid before the start of the actual reaction, or the passivation layer has to be removed, for example, by treating with hydrogen or a hydrogen-comprising gas.

Before use in the hydrogenation, the hydrogenation catalyst can be freed of the inert liquid or passivation layer. This is done, for example, by the treatment of the hydrogenation catalyst with hydrogen or a hydrogen-comprising gas. Preference is given to undertaking the hydrogenation directly after the treatment of the hydrogenation catalyst in the same reactor in which the treatment of the hydrogenation catalyst with hydrogen or a hydrogen-comprising gas was also effected.

Catalyst precursors can, however, also be used in the process without prereduction, in which case they are reduced under the conditions of the hydrogenation by the hydrogen present in the reactor, which generally forms the hydrogenation catalyst in situ.

In the process according to the invention, hydrogen is used. The hydrogen is generally used in technical grade purity. The hydrogen can also be used in the form of a hydrogen-comprising gas, i.e. in mixtures with other inert gases, such as nitrogen, helium, neon, argon or carbon dioxide. The hydrogen-comprising gases used may, for example, be reformer offgases, refinery gases, etc., if and when these gases do not comprise any catalyst poisons for the hydrogenation catalysts used, for example CO. However, preference is given to using pure hydrogen or essentially pure hydrogen in the process, for example hydrogen with a content of more than 99% by weight of hydrogen, preferably more than 99.9% by weight of hydrogen, more preferably more than 99.99% by weight of hydrogen, especially more than 99.999% by weight of hydrogen.

Additionally used in the process according to the invention are the above-described inventive mixtures comprising itaconic acid or an itaconic acid derivative and a primary amine of the formula (I)

$$R\text{—}NH_2 \qquad (I)$$

where the molar ratio of primary amine to itaconic acid or the itaconic acid derivative is in the range from 0.5:1 to 20:1, wherein the mixture comprises 50 mole percent or less of 4-carboxypyrrolidones of the formula (II), derivatives of the 4-carboxypyrrolidones of the formula (II) and 4-carbamidopyrrolidones of the formula (III), based on the itaconic acid used or the itaconic acid derivative used,

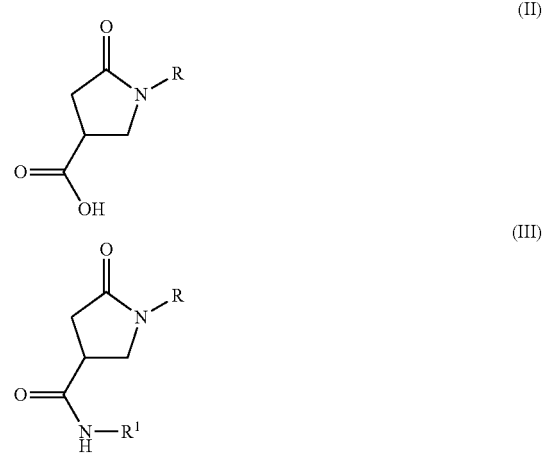

and in which R is as defined above.

The inventive mixtures preferably already comprise a solvent. In general, no further solvent is added to the inventive mixture when the mixture already comprises solvent and the proportion of itaconic acid or the itaconic acid derivative in the solvent is from 5 to 95% by weight based on the solvent used, preferably 10 to 70% by weight and more preferably 20 to 60% by weight, based in each case on the solvent used. When the proportion of itaconic acid or itaconic acid derivative is more than 95% by weight based on the solvent used, preference is given to adding a solvent to the mixture. Preference is given to adding the same solvent which has already been used to prepare the inventive mixtures.

Preferred solvents are water, methanol, ethanol, n-/isopropanol, n-/isobutanol, THF, dimethylformamide, dimethylacetamide, alkylmethylpyrrolidones or N-alkylpyrrolidones, especially water.

The hydrogenation is performed typically at a reaction pressure of 50 to 300 bar, preferably of 80 to 280 bar, more preferably of 100 to 270 bar and most preferably at a pressure of 120 to 250 bar. The pressure is maintained or controlled generally via the metered addition of hydrogen.

The hydrogenation is effected generally at reaction temperatures of 100 to 300° C., preferably 120 to 280° C., more preferably 150 to 250° C. and most preferably 180 to 220° C.

The inventive hydrogenation can be performed continuously, batchwise or semi continuously.

Suitable reactors are thus both stirred tank reactors and tubular reactors.

Typical reactors are, for example, high-pressure stirred tank reactors, autoclaves, fixed bed reactors, fluidized bed reactors, moving beds, circulating fluidized beds, salt bath reactors, plate heat exchangers as reactors, staged reactors with a plurality of stages with or without heat exchange and removal/supply of substreams between the stages, in possible embodiments as radial flow or axial flow reactors, continuous stirred tanks, bubble reactors, etc., the reactor used in each case being that suitable for the desired reaction conditions, such as temperature, pressure and residence time.

Preference is given to performing the inventive hydrogenation in a high-pressure stirred tank reactor, fixed bed reactor or fluidized bed reactor.

In the case of batchwise performance of the hydrogenation, the reaction is effected preferably in a high-pressure stirred tank reactor. In a particularly preferred embodiment, the hydrogenation is effected in the same reactor in which the inventive mixtures have been prepared. Alternatively, the inventive mixtures can be prepared in a separate reactor and be transferred to the reactor in which the hydrogenation is performed. Typically, the inventive mixtures are heated rapidly to the reaction temperature under hydrogen at a pressure of 1 to 100 bar, preferably 5 to 80 bar. In general, on attainment of the reaction temperature, the pressure is increased to the reaction pressure.

In the case of continuous performance of the hydrogenation, the reaction is effected preferably in a fixed bed reactor, in which case the inventive mixture is preferably supplied to the reaction zone in liquid form. Preference is given to heating the inventive mixture to the reaction temperature only immediately before or during its supply into the reaction zone.

The residence time in the hydrogenation—in the case of performance in a batchwise process—is generally 15 minutes to 96 hours, preferably 60 minutes to 72 hours, more preferably 2 hours to 48 hours.

In the case of performance in a continuous process, the residence time is generally 0.1 second to 24 hours, preferably 1 minute to 10 hours. For the continuous process, "residence time" in this connection means the residence time over the catalyst, and thus the residence time in the catalyst bed for a fixed bed catalyst; the synthesis part of the reactor (part of the reactor where the catalyst is localized) is considered for fluidized bed reactors.

In a preferred embodiment of the process, the residence time is selected such that the hydrogenation achieves a conversion of 99% and more, preferably 99.5% and more, more preferably 99.8% and more and especially preferably 99.9% and more, based in each case on the itaconic acid used or the itaconic acid derivative used. This preferred embodiment has the advantage that the 1,3-alkylmethylsuccinimide secondary component in the reaction mixture is hydrogenated fully to 1,3- and 1,4-alkylmethylpyrrolidone and if appropriate to 1,3-alkylmethylpyrrolidine. The formation of the 1,3-alkylmethylpyrrolidine secondary component at the expense of the 1,3-alkylmethylsuccinimide secondary component has the advantage that the 1,3-alkylmethylpyrrolidine secondary component can be removed better from the product of value (1,3-alkylmethylpyrrolidone) in a subsequent workup, especially a subsequent distillation.

Accordingly, the present invention further provides a mixture comprising 1,3-alkylmethylpyrrolidones of the general formula (VI) and/or 1,4-alkylmethylpyrrolidones of the general formula (VII) and 1,3-alkylmethylpyrrolidines of the general formula (VIII)

(VI)

(VII)

(VIII)

wherein the proportion of 1,3-alkylmethylpyrrolidines is in the range from 10 to 10 000 ppm.

The process according to the invention generally affords a reaction effluent which comprises a total of less than 2% by weight, preferably less than 1% by weight and more preferably less than 0.5% by weight of one or more secondary components selected from the group consisting of 4-carboxy-1-methylpyrrolidone, 4-carbamido-1-methylpyrrolidone, 4-hydroxymethyl-1-methylpyrrolidone and 4-methylaminomethyl-1-methylpyrrolidone.

The reaction effluent comprises a mixture of 1,3-alkylmethylpyrrolidones of the formula (VI) and 1,4-alkylmethylpyrrolidones of the formula (VII).

(VI)

(VII)

The molar ratio of 1,3-alkylmethylpyrrolidone to 1,4-alkylmethylpyrrolidone in the reaction effluent is preferably in the range from 1:1 to 10:1, more preferably 1.2:1 to 5:1, especially preferably 1.3:1 to 4:1.

Accordingly, the present invention further provides mixtures comprising 1,3-alkylmethylpyrrolidone and 1,4-alkylmethylpyrrolidone, wherein the molar ratio of 1,3-alkylmethylpyrrolidone to 1,4-alkylmethylpyrrolidone is in the range from 1:1 to 10:1.

The inventive mixtures of 1,3- and 1,4-alkylmethylpyrrolidones obtainable by means of the process according to the invention can be used as organic solvents, diluents, extractants, detergents, degreasers, adsorbents and/or dispersants, in the extraction of pure hydrocarbons in petrochemical processing, in the purification and removal of gases such as acetylene, 1,3-butadiene or isoprene, in aromatics extraction, for example in the Distapex process of LURGI GmbH, in acidic gas scrubbing and in lubricant oil extraction.

The inventive mixtures of 1,3- and 1,4-alkylmethylpyrrolidones can also be used as solvents for many polymers such as polyvinyl chloride (PVC), polyurethanes (PU), acrylates or butadiene-acrylonitrile copolymers and the processing thereof. In addition, they can be used as detergents in the removal of paint and coating residues, and as pickling agents and as detergents for metal, ceramic, glass and plastic surfaces.

The inventive mixtures of 1,3- and 1,4-alkylmethylpyrrolidones obtainable by means of the process according to the invention can likewise be used as solvents or cosolvents for the formulation of active ingredients in crop protection.

The inventive mixtures of 1,3- and 1,4-alkylmethylpyrrolidones obtainable by means of the process according to the invention can replace NMP in many applications.

The purification of the reaction effluent, for example the removal of the solvent used or of undesired by-products, can be effected by a process known to those skilled in the art, for example by distillation or rectification.

The advantages of the present invention are that it has been possible to develop stable mixtures comprising itaconic acid or an itaconic acid derivative with primary amines, which comprise only a minor proportion of undesired by-products, especially of 4-carboxypyrrolidone, derivatives of 4-carboxypyrrolidones of the formula (II) or 4-carbamidopyrrolidone.

Especially in the case of preparation of 1,3-dimethylpyrrolidone and/or 1,4-dimethylpyrrolidone, the formation of toxic N-methylpyrrolidone is very substantially avoided. N-Methylpyrrolidone can form, for example, through further reactions (decarboxylation/hydrogenation) from 4-carboxypyrrolidone.

The mixtures are stable at ambient temperature and can be stored and transported without an increased level of technical complexity.

In these mixtures, the conversion of itaconic acid or the itaconic acid derivatives to the by-products mentioned is very substantially avoided, such that the itaconic acid or derivatives thereof can react in a subsequent hydrogenation virtually completely to give the desired 1,3- and 1,4-alkylmethylpyrrolidones. The inventive mixtures are thus suitable for use in a process for preparing 1,3- and 1,4-alkylmethylpyrrolidones, in which the 1,3- and 1,4-alkylmethylpyrrolidones are obtained in high yield and selectivity based on the itaconic acid used or derivatives thereof.

The process according to the invention enables the preparation of 1,3- and 1,4-alkylmethylpyrrolidones from itaconic acid or derivatives thereof, without any need to hydrogenate the itaconic acid to 2-methylsuccinic acid in a separate reaction stage. Since the preparation of the inventive mixtures is simple to implement in technical terms, the process according to the invention for preparing 1,3- and 1,4-alkylmethylpyrrolidones has high process economy. A further advantage of this invention is that the inventive mixtures can be prepared by using itaconic acid or itaconic acid derivatives which are prepared on the basis of renewable raw materials. Reverting to renewable raw materials can contribute to sustainment of finite resources and enables sustainable economic activity.

The process according to the invention is illustrated in detail by the examples detailed below.

EXAMPLES

Analysis

The reaction effluents and distillates were analyzed by gas chromatography, optionally using a defined amount of an internal standard (diethylene glycol dimethyl ether). The mixtures were injected undiluted into the GC chromatograph (from HP, carrier gas: hydrogen) onto a 30 m DB1 column (from J+W), and analyzed at oven temperatures of 60° C. to 300° C. (heating rate 8 kelvin per minute to 220° C., then 20 kelvin per minute to 300° C.) with a flame ionization detector (temperature: 290° C.). The composition was determined by integrating the signals of the chromatogram. When an internal standard was used, the signal intensity was converted to the proportions by mass with the aid of a calibration conducted beforehand with the internal standard (diethylene glycol dimethyl ether).

The reaction mixtures were also analyzed by nuclear resonance spectroscopy. To this end, the mixtures were analyzed either diluted in a deuterated solvent ($D_2O$) or undiluted using an external standard in a spectrometer (Bruker DPX400). The quantitative ratios of the components were determined by integrating the signals in the 1H spectrum.

The determination of the water content was carried out by means of Karl-Fischer titration. To this end, 1-3 ml of the sample solution were injected into a machine for determining the water content by the Karl-Fischer method (Metrohm Karl Fischer Coulometer KF756). The measurement was effected by a coulometric route and was based on the Karl-Fischer reaction, the water-mediated reaction of iodine with sulfur dioxide.

Example 1

Itaconic acid (1.9 kg) was introduced with ice-cooling into 40% aqueous methylamine solution (2.6 l, 2.3 kg). The homogeneous solution was transferred into a 9 liter stainless steel autoclave with stirrer and admixed with the rhodium (5%)/activated carbon catalyst (98 g, moist (comprises approx. 50% water)) [source: AlfaAesar]. The autoclave was closed and hydrogen was injected to pressure 100 bar at ambient temperature. The mixture was stirred under these conditions for 2 hours. Subsequently, the mixture was heated to 200° C. and kept at this temperature for 65 hours. Further hydrogen was injected continuously, and a pressure of 250 bar was maintained. Subsequently, the autoclave was cooled, decompressed and emptied. The catalyst was removed by filtration and the crude product was analyzed by gas chromatography. The following composition (based on the organic components, i.e. disregarding water) was found:

49% 1,3-dimethylpyrrolidone
27% 1,4-dimethylpyrrolidone
8% 1,3-dimethylpyrrolidine
11% monomethylamine
2% dimethylamine
1% trimethylamine
(remainder: not identified)

4-Carboxy-1-methylpyrrolidone, 4-carbamido-1-methylpyrrolidone, 4-hydroxymethyl-1-methylpyrrolidone, 4-methylaminomethyl-1-methylpyrrolidone were not detected.
Conversion: 100%
Selectivity (based on itaconic acid): 88%

The crude product was fractionally distilled by distillation under reduced pressure in a column with random packing (length: 110 cm, diameter: 2 cm, random packings: Raschig rings, 3 mm). After the water and excess amine had been removed at atmospheric pressure, the reaction products were distilled at 4 hPa (boiling range 54-57° C. at the top of the column). All fractions which comprised >99.5% (determined by gas chromatography) of the products of value were combined.

1.1 kg of dimethylpyrrolidone (total yield 67%, isomer ratio of 1,3-dimethylpyrrolidone to 1,4-dimethylpyrrolidone 2:1) were obtained.

Example 2

Itaconic acid (0.65 kg) was introduced with ice-cooling into 40% aqueous methylamine solution (1.1 l, 0.97 kg). The homogeneous solution was transferred into a 3.5 liter stainless steel autoclave with stirrer, and admixed with the rhodium (5%)/activated carbon catalyst (33 g, dry) [source: AlfaAesar]. The autoclave was closed and hydrogen was injected to pressure 50 bar at ambient temperature. Subsequently, the mixture was heated to 200° C. and kept at this temperature for 72 hours. Further hydrogen was injected continuously and a pressure of 250 bar was maintained. Subsequently, the autoclave was cooled, decompressed and emptied. The catalyst was removed by filtration and the crude product was analyzed by gas chromatography. The following composition (based on the organic components, i.e. disregarding water) was found:
  52% 1,3-dimethylpyrrolidone
  25% 1,4-dimethylpyrrolidone
  4% 3-methylpyrrolidone
  4% 4-methylpyrrolidone
  2% 1,3-dimethylpyrrolidine
  2% monomethylamine
  1% dimethylamine
  4% trimethylamine
  2% N,N-dimethylmethylsuccinamide
  (remainder: not identified)
4-Carboxy-1-methylpyrrolidone, 4-carbamido-1-methylpyrrolidone, 4-hydroxymethyl-1-methylpyrrolidone and 4-methylaminomethyl-1-methylpyrrolidone were not detected.
Conversion: 100%
Selectivity (based on itaconic acid): 83%

Example 3

Itaconic acid (0.65 kg) was introduced with ice-cooling into 40% aqueous methylamine solution (1.1 l, 0.97 kg). The homogeneous solution was transferred into a 3.5 liter stainless steel autoclave with stirrer, and admixed with the rhodium (5%)/activated carbon catalyst (33 g, dry) [source: AlfaAesar]. The autoclave was closed and hydrogen was injected to pressure 50 bar at ambient temperature. Subsequently, the mixture was heated to 220° C. and kept at this temperature for 72 hours. Further hydrogen was injected continuously and a pressure of 250 bar was maintained. Subsequently, the autoclave was cooled, decompressed and emptied. The catalyst was removed by filtration and the crude product was analyzed by gas chromatography. The following composition (based on the organic components, i.e. disregarding water) was found:
  33% 1,3-dimethylpyrrolidone
  15% 1,4-dimethylpyrrolidone
  6% 3-methylpyrrolidone
  3% 4-methylpyrrolidone
  1% 1,3-dimethylpyrrolidine
  3% monomethylamine
  4% dimethylamine
  13% trimethylamine
  9% N,N-dimethylmethylsuccinamide
  (remainder: not identified)
4-Carboxy-1-methylpyrrolidone, 4-carbamido-1-methylpyrrolidone, 4-hydroxymethyl-1-methylpyrrolidone and 4-methylaminomethyl-1-methylpyrrolidone were not detected.
Conversion: 100%
Selectivity (based on itaconic acid): 60%

Example 4

Itaconic acid (2.0 kg) was introduced with ice-cooling into 40% aqueous methylamine solution (2.6 l, 2.3 kg). The homogeneous solution was transferred into a 9 liter stainless steel autoclave with stirrer and admixed with rhodium (5%)/activated carbon catalyst which had already been used for the synthesis of DMP and fiiltered off after the end of the reaction (98 g, moist, approx. 50% water) [source: AlfaAesar]. The autoclave was closed and hydrogen was injected to pressure 100 bar at ambient temperature. After 2 hours, the mixture was heated to 200° C. and kept at this temperature for 65 hours. Further hydrogen was injected continuously, and a pressure of 200 bar was maintained. Subsequently, the autoclave was cooled, decompressed and emptied. The catalyst was removed by filtration and the crude product was analyzed by gas chromatography. The following composition (based on the organic components, i.e. disregarding water) was found:
  54% 1,3-dimethylpyrrolidone
  29% 1,4-dimethylpyrrolidone
  1% 3-methylpyrrolidone
  7% 1,3-dimethylpyrrolidine
  6% monomethylamine
  2% dimethylamine
  1% trimethylamine
  (remainder: not identified)
4-Carboxy-1-methylpyrrolidone, 4-carbamide-1-methylpyrrolidone, 4-hydroxymethyl-1-methylpyrrolidone and 4-methylaminomethyl-1-methylpyrrolidone were not detected.
Conversion: 100%
Selectivity (based on itaconic acid): 91%

Example 5

Itaconic acid (26 g) was introduced with ice-cooling into 40% aqueous methylamine 15, solution (18 ml, 16 g) and diluted with water (23 ml). The homogeneous solution was transferred into a 300 milliliter stainless steel autoclave with stirrer and admixed with the ruthenium (5%)/activated carbon catalyst (1.3 g, dry) [source: AlfaAesar]. The autoclave was closed and hydrogen was injected to pressure 50 bar at ambient temperature. Subsequently, the mixture was heated to 200° C. and kept at this temperature for 24 hours. Further hydrogen was injected continuously and a pressure of 200 bar was maintained. Subsequently, the autoclave was cooled, decompressed and emptied. The catalyst was removed by filtration and the crude product was analyzed by gas chromatography. The following composition (based on the organic components, i.e. disregarding water) was found:
- 15% 1,3-dimethylpyrrolidone
- 7% 1,4-dimethylpyrrolidone
- 5% 3-methylpyrrolidone
- 3% 4-methylpyrrolidone
- 1% N,N-dimethylmethylsuccinamide
- (remainder: not identified)

4-Carboxy-1-methylpyrrolidone, 4-carbamide-1-methylpyrrolidone, 4-hydroxymethyl-1-methylpyrrolidone and 4-methylaminomethyl-1-methylpyrrolidone were not detected.
Conversion: 100%
Selectivity (based on itaconic acid): 21%

Example 6

Itaconic acid (52 g) was introduced with ice-cooling into 40% aqueous methylamine solution (87 ml, 78 g). The homogeneous solution was transferred into a 300 milliliter stainless steel autoclave with stirrer and admixed with the ruthenium (5%)/activated carbon catalyst (2.6 g, dry) [source: AlfaAesar]. The autoclave was closed and hydrogen was injected to pressure 100 bar at ambient temperature. Subsequently, the mixture was heated to 200° C. and kept at this temperature for 65 hours. Further hydrogen was injected continuously and a pressure of 200 bar was maintained. Subsequently, the autoclave was cooled, decompressed and emptied. The catalyst was removed by filtration and the crude product was analyzed by gas chromatography. The following composition (based on the organic components, i.e. disregarding water) was found:
- 55% 1,3-dimethylpyrrolidone
- 23% 1,4-dimethylpyrrolidone
- 7% 1,3-dimethylpyrrolidine
- 3% monomethylamine
- 2% dimethylamine
- 6% trimethylamine
- 3% 3-methylpyrrolidone
- 1% 4-methylpyrrolidone
- (remainder: not identified)

4-Carboxy-1-methylpyrrolidone, 4-carbamide-1-methylpyrrolidone, 4-hydroxymethyl-1-methylpyrrolidone and 4-methylaminomethyl-1-methylpyrrolidone were not detected.
Conversion: 100%
Selectivity (based on itaconic acid): 88%

Comparative Example 1

Procedure as example 6, except that the reaction was kept at 100° C. over the entire running time of the hydrogenation reaction.
The following composition (based on the organic components, i.e. disregarding water) was found:
- 0% 1,3-dimethylpyrrolidone
- 0% 1,4-dimethylpyrrolidone
- 7% 1,3-dimethylsuccinimide
- 34% monomethylamine
- 8% trimethylamine
- 35% methylsuccinic acid
- 3% 4-carboxy-1-methylpyrrolidone
- 7% N,N-dimethylmethylsuccinamide
- (remainder: not identified)

Conversion: 100%
Selectivity (based on itaconic acid): 0%

Comparative Example 2

Procedure as example 6, except that the starting mixture used was a solution of 4-carboxy-1-methylpyrrolidone (20 g), which had been obtained by contacting methylamine and itaconic acid at temperatures of more than 100° C. (prepared in analogy to comparative example 4) in water (80 g), and also rhodium (5%)/activated carbon (1 g).
The following composition (based on the organic components, i.e. disregarding water) was found after 65 hours:
- 40% 1,3-dimethylpyrrolidone
- 24% 1,4-dimethylpyrrolidone
- 3% N-methylpyrrolidone (NMP)
- 16% 1,3-dimethylsuccinimide
- 2% 4-carboxy-1-methylpyrrolidone
- 7% 4-hydroxymethyl-1-methylpyrrolidone
- 1% 4-carbamide-1-methylpyrrolidone
- (remainder: not identified)

Conversion: 98%
Selectivity (based on itaconic acid): 65%

Example 7

Itaconic acid (32 g) was introduced with ice-cooling into 40% aqueous methylamine solution (43 ml, 39 g). The homogeneous solution was transferred into a 100 milliliter stainless steel autoclave with stirrer and admixed with the rhodium (5%)/activated carbon catalyst (1.6 g, dry, 5% by weight based on itaconic acid) [source: AlfaAesar]. The autoclave was closed and hydrogen was injected to pressure 50 bar at ambient temperature. Subsequently, the mixture was heated to 200° C. and kept at this temperature for 24 hours. Further hydrogen was injected continuously and a pressure of 200 bar was maintained. Subsequently, the autoclave was cooled, decompressed and emptied. The catalyst was removed by filtration and the crude product was analyzed by gas chromatography. The following composition (based on the organic components, i.e. disregarding water) was found:
- 49% 1,3-dimethylpyrrolidone
- 18% 1,4-dimethylpyrrolidone
- 8% 1,3-dimethylsuccinimide
- 1% 1,3-dimethylpyrrolidine
- 4% monomethylamine
- 1% dimethylamine
- <1% trimethylamine
- 1% 3-methylpyrrolidone
- 1% 4-methylpyrrolidone
- (remainder: not identified)

4-Carboxy-1-methylpyrrolidone, 4-carbamide-1-methylpyrrolidone, 4-hydroxymethyl-1-methylpyrrolidone and 4-methylaminomethyl-1-methylpyrrolidone were not detected.
Conversion: 100%
Selectivity (based on itaconic acid): 71%

Example 8

Preparation of the Feed Mixture at 50° C.

Itaconic acid (18.5 g; 0.142 mol) was added slowly and in portions with waterbath cooling to an aqueous solution of methylamine (41% in water, 21.5 g based on the aqueous solution, 0.284 mol, 2.0 equivalents), in such a way that the temperature always remained below 50° C. during the mixing operation. The mixture was subsequently stirred at 50° C. for 1 hour. The composition of the mixture was analyzed by ¹H NMR (solvent: D₂O as an external standard) on the basis of the olefinic signals of itaconic acid (present as the ammonium salt) (chemical shifts 5.3 ppm and 5.7 ppm) and of the signals of the methylene function beside the nitrogen atom of the 4-carboxy-1-methylpyrrolidone (chemical shift 3.6-3.8 ppm). The itaconic acid:4-carboxy-1-methylpyrrolidone ratio was 100:0.

Example 9

Preparation of the Feed Mixture at 100° C.

Itaconic acid and methylamine were mixed as described in example 8 and then heated to 100° C. for 1 hour. NMR analysis showed that the itaconic acid:4-carboxy-1-methylpyrrolidone ratio was 76:24.

Comparative Example 3

Preparation of the Feed Mixture at 150° C.

Itaconic acid and methylamine were mixed as described in example 8 and then heated to 150° C. for 1 hour. NMR analysis showed that the itaconic acid:4-carboxy-1-methylpyrrolidone ratio was 0:100.

Example 10

Preparation of the 1:1 Itaconic Acid/Methylamine Feed Mixture at 50° C.

Itaconic acid (18.5 g; 0.142 mol) and methylamine (41% in water, 10.7 g based on the aqueous solution, 0.142 mol, 1.0 equivalent) were mixed as in example 8. In addition, the addition of 20 ml of water was required in order to prevent formation of precipitate at 50° C. NMR analysis showed that the itaconic acid:4-carboxy-1-methylpyrrolidone ratio was 100:0.

Comparative Example 4

Preparation of the 1:1 Itaconic Acid/Methylamine Feed Mixture at Boiling Temperature Itaconic acid (100 g, 0.78 mol) and methylamine (41% in water, 60.0 g based on the aqueous solution, 0.80 mol, 1.0 equivalent) were mixed as in example 8. The suspension was heated to boiling under reflux at standard pressure for 1 hour (in the course of which the boiling point rises to approx. 115° C.). This dissolved the solids completely. Cooling to ambient temperature formed a precipitate. NMR analysis of the homogeneous solution and of the precipitated crystals (solvent: D₂O) showed that the itaconic acid:4-carboxy-1-methylpyrrolidone ratio in both phases was 0:100. The 4-carboxy-1-methylpyrrolidone product was purified by recrystallization from ethyl acetate and was obtained in the form of colorless crystals (yield: 59 g, 67%).

The invention claimed is:

1. A process for preparing 1,3-alkylmethylpyrrolidone of the general formula (VI) and/or 1,4-alkylmethylpyrrolidone of the general formula (VII)

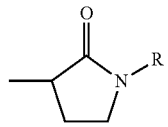 (VI)

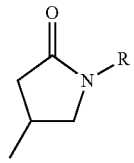 (VII)

which comprises reacting a mixture comprising itaconic acid or an itaconic acid derivative and a primary amine of the formula (I) with hydrogen in the presence of a hydrogenation catalyst

R—NH₂ (I)

where the molar ratio of primary amine to itaconic acid or the itaconic acid derivative is in the range from 0.5:1 to 20:1 and the mixture comprises 50 mole percent or less of 4-carboxypyrrolidones of the formula (II), derivatives of the 4-carboxypyrrolidones of the formula (II) and 4-carbamidopyrrolidones of the formula (III), based on itaconic acid or itaconic acid derivative,

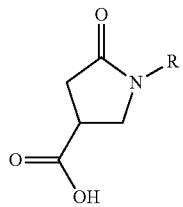 (II)

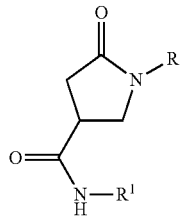 (III)

and

R is a linear or branched saturated aliphatic radical having 1 to 24 carbon atoms or a saturated cycloaliphatic radical having 3 to 24 carbon atoms.

2. The process for preparing alkylmethylpyrrolidone according to claim 1, wherein the temperature is within a range from 100 to 300° C. and the pressure is within a range from 50 to 300 bar.

3. The process for preparing alkylmethylpyrrolidone according to claim 1, wherein the hydrogenation catalyst comprises rhodium, ruthenium or cobalt.

4. The process for preparing alkylmethylpyrrolidone according to claim 1, wherein the product mixture comprises less than 1% N-methylpyrrolidone as a by-product.

5. The process for preparing alkylmethylpyrrolidone according to claim 1, wherein the conversion based on the itaconic acid used or the itaconic acid derivative used is 99% and more.

6. A mixture comprising 1,3-alkylmethylpyrrolidone of the general formula (VI) and 1,4-alkylmethylpyrrolidone of the general formula (VII)

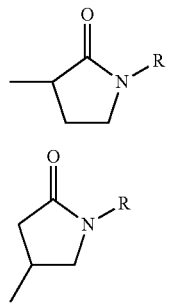

(VI)

(VII)

wherein the molar ratio of 1,3-alkylmethylpyrrolidone to 1,4-alkylmethylpyrrolidone is in the range from 1:1 to 10:1 and R is a linear or branched saturated aliphatic radical having 1 to 24 carbon atoms or a saturated cycloaliphatic radical having 3 to 24 carbon atoms.

7. A mixture comprising 1,3-alkylmethylpyrrolidones of the general formula (VI) and/or 1,4-alkylmethylpyrrolidones of the general formula (VII) and 1,3 alkylmethylpyrrolidines of the general formula (VIII)

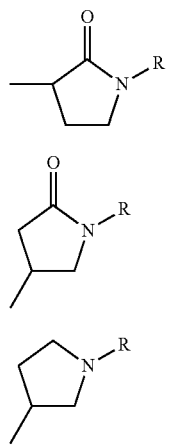

(VI)

(VII)

(VIII)

where the proportion of 1,3-alkylmethylpyrrolidines is in the range from 10 to 10 000 ppm and R is a linear or branched saturated aliphatic radical having 1 to 24 carbon atoms or a saturated cycloaliphatic radical having 3 to 24 carbon atoms.

8. A process for preparing the mixture according to claim 7, which comprises reacting a mixture comprising itaconic acid or an itaconic acid derivative and a primary amine of the formula (I) with hydrogen in the presence of a hydrogenation catalyst $R-NH_2$ (I)

where the molar ratio of primary amine to itaconic acid or the itaconic acid derivative is in the range from 0.5:1 to 20:1 and the mixture comprises 50 mole percent or less of 4-carboxypyrrolidones of the formula (II), derivatives of the 4-carboxypyrrolidones of the formula (II) and 4-carbamidopyrrolidones of the formula (III), based on itaconic acid or itaconic acid derivative,

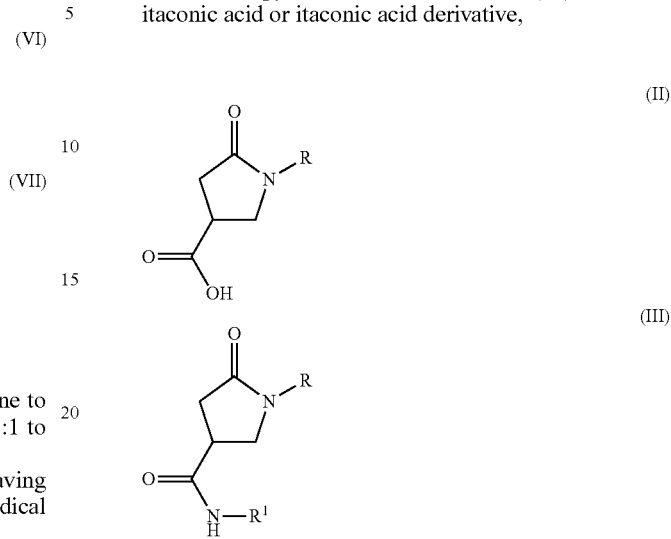

(II)

(III)

and

R is a linear or branched saturated aliphatic radical having 1 to 24 carbon atoms or a saturated cycloaliphatic radical having 3 to 24 carbon atoms and wherein the hydrogenation achieves a conversion of 99% and more, based on the itaconic acid used or the itaconic acid derivative used.

9. A solvent, diluent, extractant, detergent, degreaser, adsorbent and/or dispersant, in the extraction of pure hydrocarbons in petrochemical processing, in the purification and removal of gases, in aromatics extraction, in acidic gas scrubbing and in lubricant oil extraction, as a solvent for polymers, as a detergent in the removal of paint and coating residues, as a pickling agent and as a detergent for metal, ceramic, glass and plastic surfaces, as a solvent or cosolvent for the formulation of active ingredients in crop protection and as a replacement for NMP which comprises the mixture according to claim 6.

10. The process for preparing alkylmethylpyrrolidone according to claim 1, wherein the mixture comprises 10 mole percent or less of 4-carboxypyrrolidones of the formula (II), derivatives of the 4-carboxypyrrolidones of the formula (II), and 4-carbamidopyrrolidones of the formula (III).

11. The process for preparing alkylmethylpyrrolidone according to claim 1, wherein the mixture comprises 5 mole percent or less of 4-carboxypyrrolidones of the formula (II), derivatives of the 4-carboxypyrrolidones of the formula (II), and 4-carbamidopyrrolidones of the formula (III).

12. The process for preparing alkylmethylpyrrolidone according to claim 1, wherein the mixture comprises 1 mole percent or less of 4-carboxypyrrolidones of the formula (II), derivatives of the 4-carboxypyrrolidones of the formula (II), and 4-carbamidopyrrolidones of the formula (III).

13. The process for preparing alkylmethylpyrrolidone according to claim 1, wherein the hydrogenation catalyst comprises rhodium.

* * * * *